United States Patent
Sauer

(10) Patent No.: US 9,554,781 B2
(45) Date of Patent: Jan. 31, 2017

(54) MINIMALLY INVASIVE SURGICAL SUTURING DEVICE AND METHOD

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

(*) Notice: Subject to any disclaimer, the term of this patent is extended or adjusted under 35 U.S.C. 154(b) by 305 days.

(21) Appl. No.: 14/161,793

(22) Filed: Jan. 23, 2014

(65) Prior Publication Data
US 2015/0201926 A1 Jul. 23, 2015

(51) Int. Cl.
A61B 17/04 (2006.01)
A61B 17/00 (2006.01)
A61B 17/062 (2006.01)

(52) U.S. Cl.
CPC ..... *A61B 17/00234* (2013.01); *A61B 17/0469* (2013.01); *A61B 17/0625* (2013.01); *A61B 2017/00398* (2013.01)

(58) Field of Classification Search
CPC ............ A61B 17/0469; A61B 17/0482; A61B 17/0483; A61B 17/0057; A61B 2017/00663; A61B 2017/00637; A61B 2017/00641; A61B 17/00234
USPC ................................. 606/139, 144–148, 224
See application file for complete search history.

(56) References Cited

U.S. PATENT DOCUMENTS

| | | | |
|---|---|---|---|
| 5,423,858 A * | 6/1995 | Bolanos ............. | A61B 17/0057 24/297 |
| 5,431,666 A | 7/1995 | Sauer | |
| 5,562,686 A * | 10/1996 | Sauer ................ | A61B 17/0469 112/169 |
| 5,575,800 A | 11/1996 | Gordon | |
| 5,578,044 A | 11/1996 | Gordon | |
| 5,674,230 A * | 10/1997 | Tovey ............... | A61B 17/0469 606/139 |
| 5,700,272 A | 12/1997 | Gordon | |
| 5,741,279 A | 4/1998 | Gordon | |
| 5,766,183 A | 6/1998 | Sauer | |
| 5,879,371 A * | 3/1999 | Gardiner ........... | A61B 17/0469 606/144 |
| 6,051,006 A * | 4/2000 | Shluzas ............. | A61B 17/0469 606/144 |
| 6,368,334 B1 | 4/2002 | Sauer | |
| 6,533,796 B1 | 3/2003 | Sauer | |
| 6,641,592 B1 | 11/2003 | Sauer | |
| 6,997,931 B2 | 2/2006 | Sauer | |

(Continued)

*Primary Examiner* — Todd E Manahan
*Assistant Examiner* — Charles Wei
(74) *Attorney, Agent, or Firm* — Christopher B. Miller

(57) ABSTRACT

A minimally invasive surgical suturing device has a shaft; a needle slideably coupled to the shaft and having a ferrule engaging end; and a guide tip having a ferrule receiving aperture and moveably coupled to the shaft for selectable movement between a retracted position and an enabled position. In a related method, a distal shaft end, having a guide tip in a retracted position, is passed through a minimally invasive entry point and into a body cavity. The guide tip having a ferrule receiving aperture is actuated into an enabled position such that an insertion profile of the guide tip and shaft in the enabled position is larger than an access dimension of the minimally invasive entry point. A needle, slideably coupled to the shaft and having a ferrule engaging end, is advanced on a path substantially parallel to the shaft, toward and in alignment with the ferrule receiving aperture.

5 Claims, 10 Drawing Sheets

(56) References Cited

U.S. PATENT DOCUMENTS

| | | | |
|---|---|---|---|
| 7,211,093 B2 | 5/2007 | Sauer | |
| 7,407,505 B2 | 8/2008 | Sauer | |
| 7,731,727 B2 | 6/2010 | Sauer | |
| 8,123,762 B2 * | 2/2012 | Chu | A61B 17/0469 606/144 |
| 8,313,496 B2 | 11/2012 | Sauer | |
| 8,398,657 B2 | 3/2013 | Sauer | |
| 8,591,528 B2 | 11/2013 | Devens | |
| 8,652,149 B2 | 2/2014 | Sauer | |
| 8,679,136 B2 * | 3/2014 | Mitelberg | A61B 1/00087 606/144 |
| 2009/0036906 A1 * | 2/2009 | Stafford | A61B 17/0057 606/144 |
| 2009/0222027 A1 | 9/2009 | Sauer | |
| 2011/0082475 A1 * | 4/2011 | Smith | A61B 17/0057 606/144 |
| 2012/0016383 A1 | 1/2012 | Sauer | |
| 2012/0143248 A1 | 6/2012 | Brecher | |
| 2012/0221022 A1 * | 8/2012 | Devens, Jr. | A61B 17/0469 606/144 |

\* cited by examiner

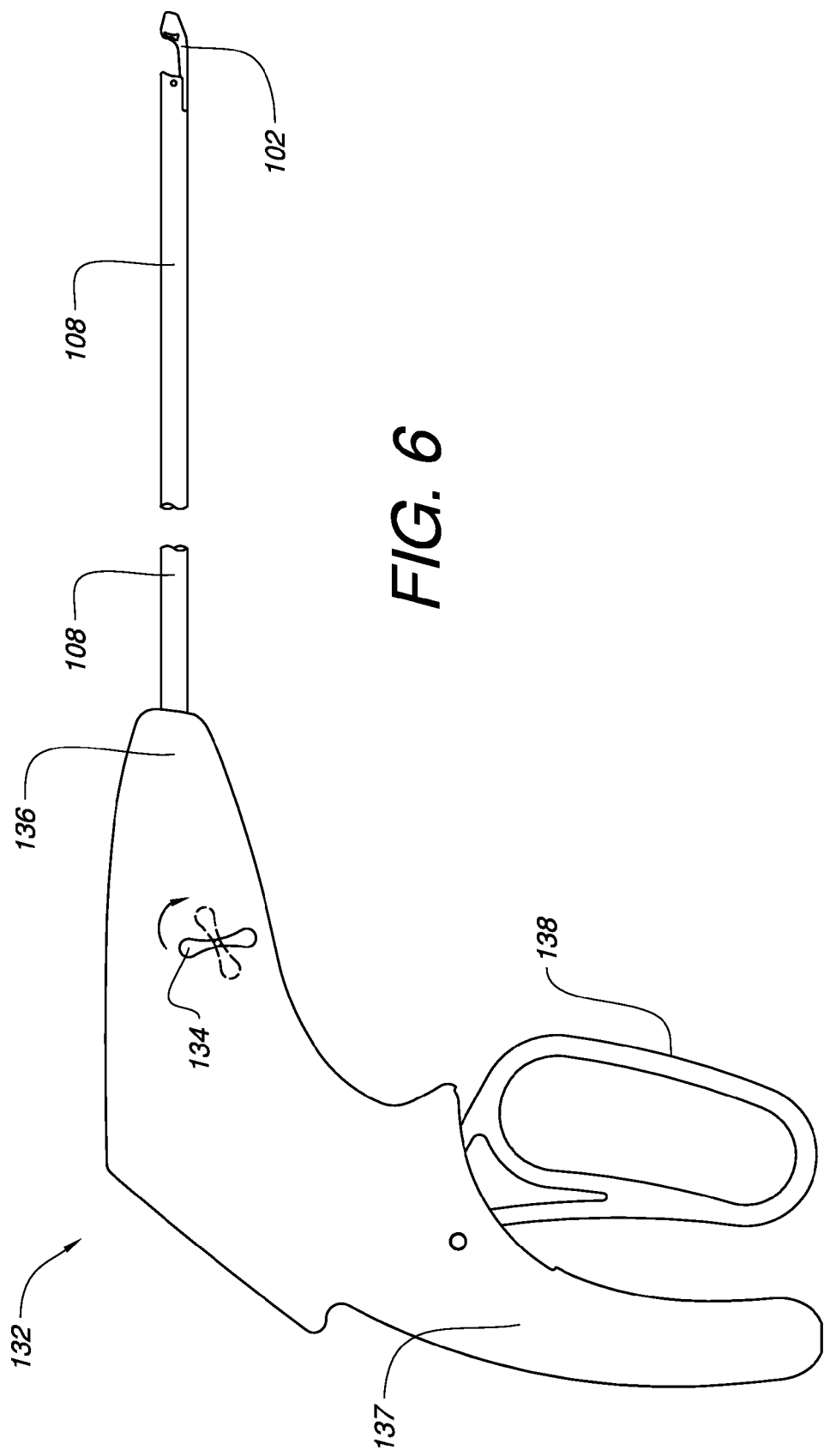

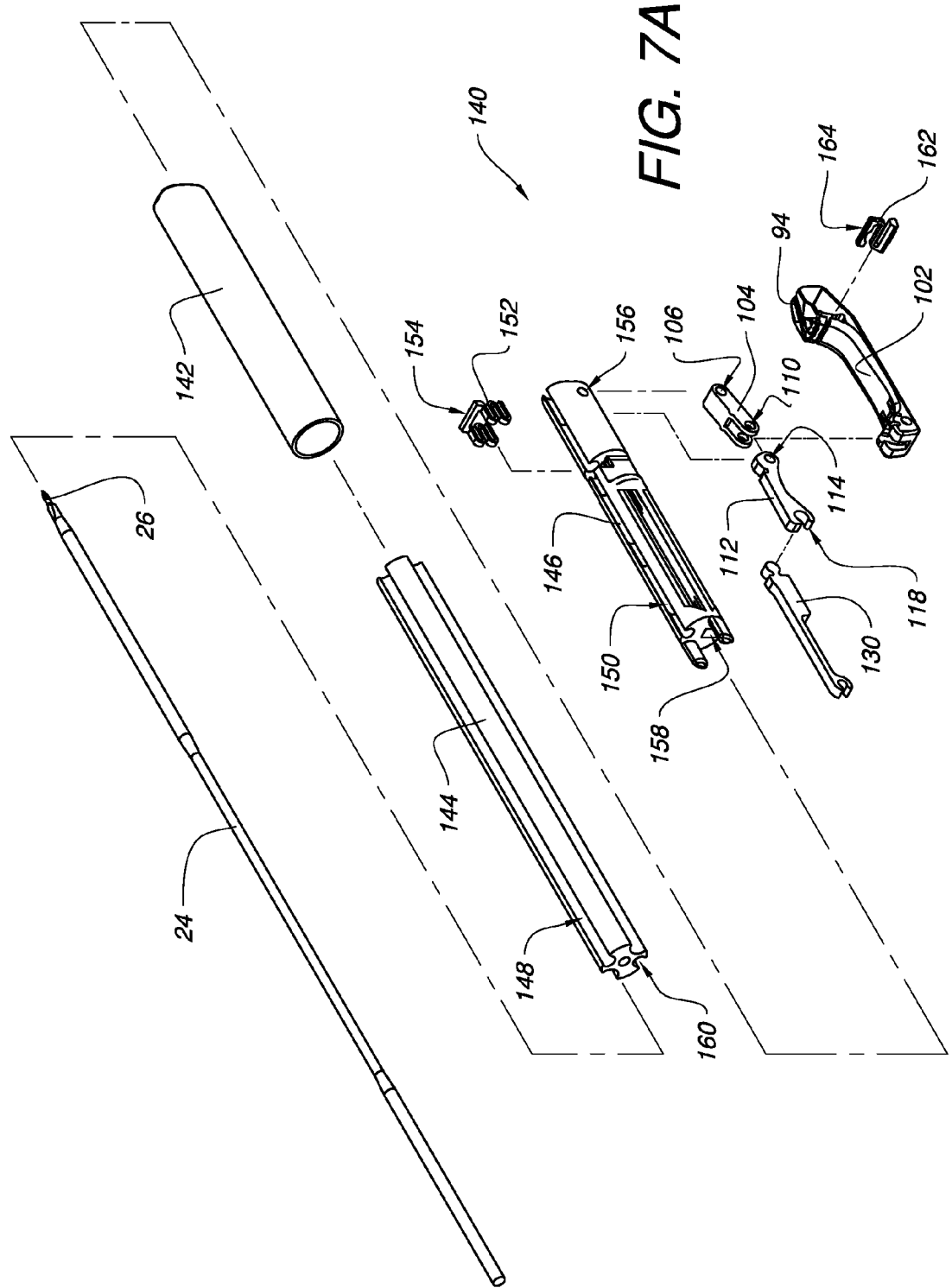

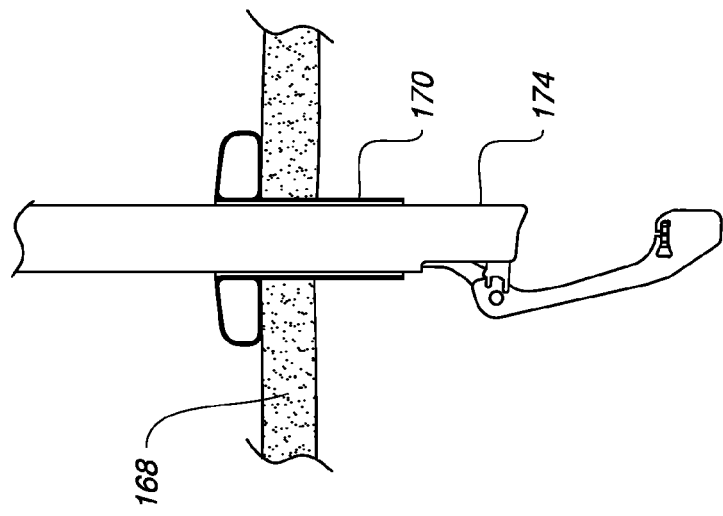
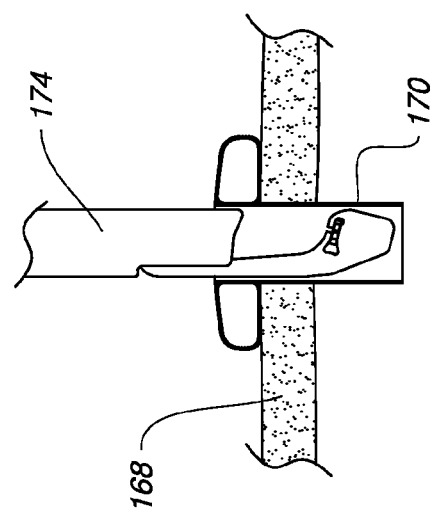
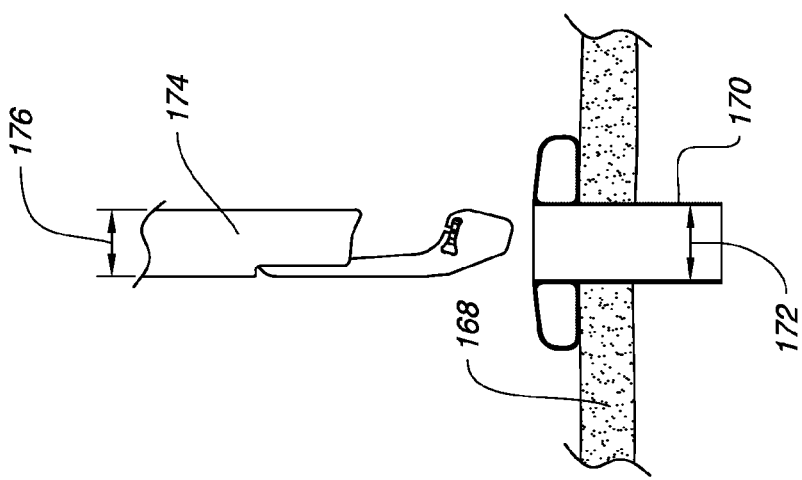

MINIMALLY INVASIVE SURGICAL SUTURING DEVICE AND METHOD

FIELD

The claimed invention relates to surgical suturing, and more specifically to minimally invasive surgical suturing devices and methods.

BACKGROUND

Minimally invasive surgery (MIS) has allowed physicians to carry out many surgical procedures with less pain and disability than conventional, open surgery. However, unlike conventional open surgery, where the surgical site is readily accessible through a large incision, MIS typically requires the surgeon to operate remotely by inserting and manipulating instruments through small punctures, openings, or access sites in the body wall. A hollow cannula may be placed in the puncture to create a minimally invasive entry point. The cannulas, typically ranging in size from 5 to 20 millimeters (mm) are often sealed to maintain positive pressure within the peritoneal cavity to facilitate pneumoperitoneum during laparascopic surgery. One or more cannulas may be inserted into the body for any given operation. Medical instruments, such as grippers, manipulators, cutters, and suturing (sewing) devices are then inserted through the one or more cannula.

One of the more problematic tasks in MIS is suturing. Some surgeons use manipulators, such as needle drivers and gripping clamps, through an MIS entry point, as an extension of their hands in MIS suturing. Such techniques are time consuming and often require coordinated manipulation of multiple instruments. Given the limited space, limited visualization, and limited mobility in MIS, many surgeons find minimally invasive suturing by hand an extremely slow and difficult surgical task.

In response to the MIS suturing difficulties faced by surgeons, suturing devices have been developed to assist with and partially automate the rapid placement of suture stitches. Such devices often are available in a variety of sizes to fit through a corresponding variety of cannula openings. Larger MIS suturing devices can be effective in closing wounds because they are able to engage a larger bite of tissue for suturing, thereby enabling deeper suture placement within the tissue, and minimizing the likelihood that the suture will pull through the tissue. This can lead surgeons to choose larger cannula sizes, such as 10 mm or larger, in order to accommodate the larger suturing tools. Larger cannula sizes are associated with problems such as post-operative hernia formation or pain. Smaller cannulas, such as 5 mm, can lead to better patient outcomes including less peri-operative pain, rapid return of normal functions, earlier return to home and work, and reduced herniation risk. Unfortunately, currently available MIS suturing devices force a surgeon to trade-off between minimizing an invasive entry point size and maximizing suturing device effectiveness.

Therefore, there is a need for an efficient and precise minimally invasive surgical suturing device that enables surgeons to utilize small access sites without sacrificing the optimal larger tissue engagement features needed to enhance suturing effectiveness.

SUMMARY

A minimally invasive surgical suturing device is disclosed. The surgical suturing device has a shaft. The surgical suturing device also has a needle slideably coupled to the shaft and having a ferrule engaging end. The surgical suturing device further has a guide tip having a ferrule receiving aperture and moveably coupled to the shaft for selectable movement between a retracted position and an enabled position.

Another minimally invasive surgical suturing device is disclosed. The surgical suturing device has a shaft. The surgical suturing device also has a needle slideably coupled to the shaft and having a ferrule engaging end. The surgical suturing device further has a guide tip having a tissue engaging surface and a ferrule receiving aperture, the guide tip moveably coupled to the shaft for selectable movement between a retracted position and an enabled position. The surgical suturing device also has a linkage moveably coupling the guide tip to the shaft. The linkage has 1) a drive yoke pivotally coupled at a first end to the shaft and pivotally coupled at a second end to the guide tip; 2) a drive link pivotally coupled at a first end to the point where the drive yoke and the guide tip are pivotally coupled; and 3) an actuator coupled to a second end of the drive link. The ferrule receiving aperture of the guide tip is not aligned with a movement path of the ferrule engaging end of the needle when the guide tip is in the retracted position. The ferrule receiving aperture of the guide tip is aligned with the movement path of the ferrule engaging end of the needle when the guide tip is in the enabled position. The tissue engaging surface of the guide tip defines a tissue bite area in conjunction with the movement path of the ferrule engaging end of the needle. The tissue bite area is larger when the guide tip is in the enabled position than when the guide tip is in the retracted position. A movement of the actuator that pushes the second end of the drive link toward the guide tip causes the guide tip to move toward the enabled position when starting in the retracted position. A movement of the actuator that pulls the second end of the drive link away from the guide tip causes the guide tip to move toward the retracted position when starting in the enabled position.

A minimally invasive surgical suturing method is also disclosed. A distal end of a shaft, having a guide tip in a retracted position, is passed through a minimally invasive entry point and into a body cavity. The guide tip having a ferrule receiving aperture is actuated into an enabled position such that an insertion profile of the guide tip and shaft in the enabled position is larger than an access dimension of the minimally invasive entry point. A needle, slideably coupled to the shaft and having a ferrule engaging end, is advanced on a path substantially parallel to the shaft, toward and in alignment with the ferrule receiving aperture.

BRIEF DESCRIPTION OF THE DRAWINGS

FIG. 6 illustrates an embodiment of a minimally invasive surgical suturing device having another embodiment of an actuator for moving a guide tip between retracted and engaged positions.

FIG. 7A is an exploded perspective view of another embodiment of a minimally invasive surgical suturing device.

FIGS. 8A-8C schematically illustrate one embodiment of passing of a distal end of a minimally invasive surgical suturing device's shaft, having a guide tip in a retracted position, through a minimally invasive entry point and into a body cavity where the guide tip is actuated into an enabled position.

Figure 1A:
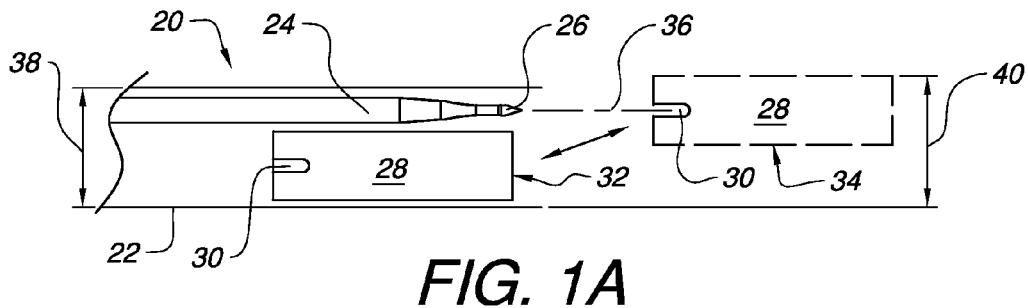
FIGS. 1A-1C schematically illustrate embodiments of a minimally invasive surgical suturing device having a guide tip, with a ferrule receiving aperture, moveably coupled to a shaft for selectable movement between a retracted position and an enabled position.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

A minimally invasive surgical device may be configured to have a shaft which is sized to be passable from outside a body, through a cannula, and into a body cavity. The shaft may couple a handle or grip on a proximal end of the shaft to a surgical tool on a distal end of the shaft. The handle or grip may have one or more controls which can be manipulated in conjunction with moving the handle to direct and control the placement and functionality of the surgical tool on the distal end when the distal end of the shaft is inside the body cavity.

FIG. 1A schematically illustrates one embodiment of a minimally invasive surgical suturing device 20. In particular, FIG. 1A focuses on the distal end of the minimally invasive surgical suturing device 20. The surgical suturing device 20 has a shaft 22. Depending on the embodiment, the shaft 22 may be rigid, flexible, or a combination thereof and may be constructed from one or more of a variety of materials, including, but not limited to metals and plastics. The shaft 22 may have a constant cross-section or a varying cross-section. Similarly, the shaft 22 may have one or more of a variety of cross-sectional shapes, including, but not limited to circular, octagonal, triangular, square, oval, symmetrical, and non-symmetrical.

The minimally invasive surgical suturing device 20 has a needle 24 which is slideably coupled to the shaft and has a ferrule engaging end 26. The needle 24 is preferably slideable in directions substantially parallel to the shaft 22. The suturing device 20 also has a guide tip 28 having a ferrule receiving aperture 30. The guide tip 28 is moveably coupled to the shaft 22 for selectable movement between a retracted position 32 and an enabled position 34. The ferrule receiving aperture 30 of the guide tip 28 is aligned with a movement path 36 of the ferrule engaging end 26 of the needle 24 when the guide tip 28 is in the enabled position 34. The ferrule receiving aperture 30 of the guide tip 28 is not aligned with the movement path 36 of the ferrule engaging end 26 of the needle 24 when the guide tip 28 is in the retracted position 32.

The ferrule engaging end 26 of the needle 24 and the ferrule receiving aperture 30 may be configured, as is known to those skilled in the art, to cooperate with a suture having a ferrule attached to one end. As one non-limiting example, U.S. Pat. No. 7,211,093 to Jude S. Sauer, et al. discloses a needle having a ferrule engaging tip which is reciprocally movable across a gap. A ferrule receiving aperture is permanently located at a distal end of the gap for selectively holding and releasing a ferrule attached to a suture so that, in a first mode, the needle engages the ferrule and draws the suture across the gap. In a second mode, the needle moves the suture ferrule back across the gap to the ferrule receiving aperture and the needle separates from the suture ferrule as the needle is retracted back across the gap, leaving the suture ferrule in the aperture. U.S. Pat. No. 7,211,093 is hereby incorporated by reference in its entirety.

Referring again to FIG. 1A, alignment of the ferrule receiving aperture 30 with the movement path 36 of the ferrule engaging end 26 of the needle 24 is critical for minimally invasive suturing using such a device. However, the surgical suturing embodiments disclosed herein, as well as their equivalents, have the advantage of being able to adjust the position of the guide tip 28 between a retracted position 32 and an enabled position 34. As pointed out, when the guide tip 28 is in the enabled position, the ferrule receiving aperture 30 of the guide tip 28 is aligned with a movement path 36 of the ferrule engaging end 26 of the needle 24. When the guide tip 28 is in the retracted position 32, however, the movement path 36 of the ferrule engaging end 26 of the needle 24 does not necessarily need to be aligned with the ferrule receiving aperture 30. This enables the suturing device 20 to have smaller insertion profile 38 when the guide tip 28 is in the refracted position 32, than the insertion profile 40 corresponding to when the guide tip 28 is in the enabled position 34.

Figure 1B:
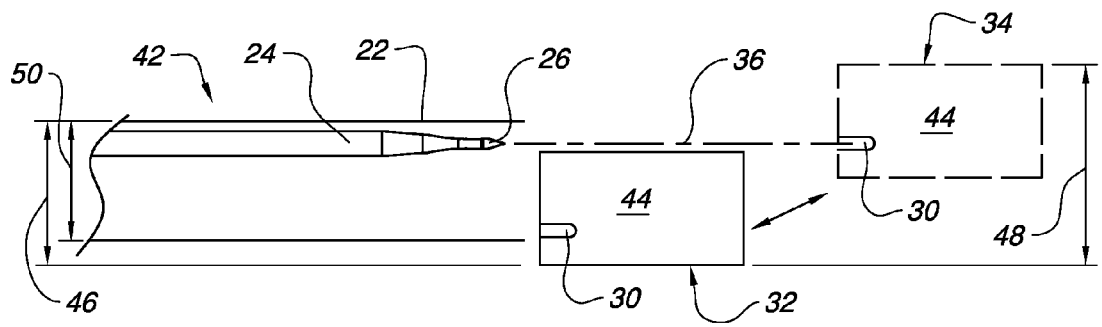

FIG. 1B schematically illustrates another embodiment of a minimally invasive surgical suturing device 42. The suturing device 42 has a shaft 22. The suturing device 42 also has a needle 24 which is slideably coupled to the shaft 22 and has a ferrule engaging end 26. The needle 24 is preferably slideable in directions substantially parallel to the shaft 22. The suturing device 42 also has a guide tip 44 having a ferrule receiving aperture 30. The guide tip 44 is moveably coupled to the shaft 22 for selectable movement between a retracted position 32 and an enabled position 34. The ferrule receiving aperture 30 of the guide tip 44 is aligned with a movement path 36 of the ferrule engaging end 26 of the needle 24 when the guide tip 44 is in the enabled position 34. The ferrule receiving aperture 30 of the guide tip 44 is not aligned with the movement path 36 of the ferrule engaging end 26 of the needle 24 when the guide tip 44 is in the retracted position 32.

The ferrule engaging end 26 of the needle 24 and the ferrule receiving aperture 30 may be configured to cooperate with a suture having a ferrule attached to one end as described previously. As with the previous embodiment, the device 42 of FIG. 1B has a smaller insertion profile 46 when the guide tip 44 is in the retracted position 32, than the insertion profile 48 corresponding to when the guide tip 44 is in the enabled position 34. As with previous embodiments, since the insertion profile 46 is smaller in the refracted position 32 than the insertion profile 48 in the engaged position, the device 42 can be used with a smaller minimally invasive entry point than would be required for a non-retractable device. In some embodiments, such as the embodiment of FIG. 1B, the insertion profile 46 when the guide tip 44 is retracted is larger than an insertion profile 50 of the shaft 22 alone. In other embodiments, such as the embodiment of FIG. 1A, the insertion profile 38 when the guide tip 28 is retracted is no larger than the insertion profile of the shaft 22 alone.

Figure 1C:
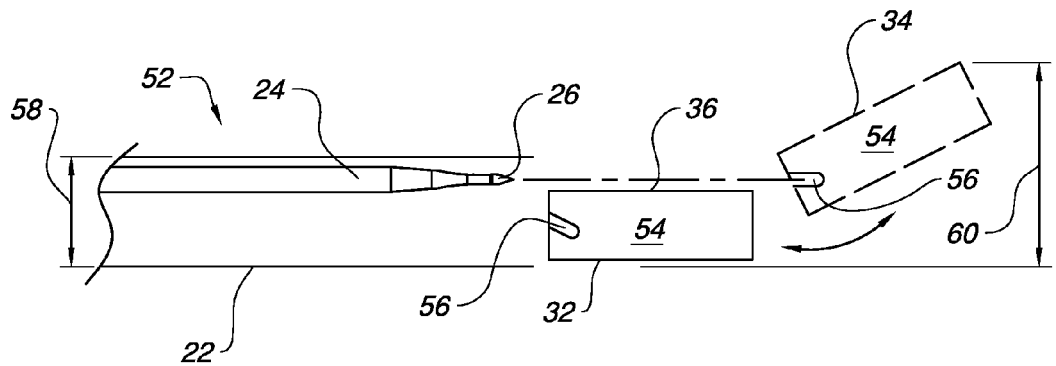

FIG. 1C schematically illustrates another embodiment of a minimally invasive surgical suturing device 52. The suturing device 52 has a shaft 22. The suturing device 52 also has a needle 24 which is slideably coupled to the shaft 22 and has a ferrule engaging end 26. The needle 24 is preferably slideable in directions substantially parallel to the shaft 22. The suturing device 52 also has a guide tip 54 having a ferrule receiving aperture 56. The guide tip 54 is moveably coupled to the shaft 22 for selectable movement between a retracted position 32 and an enabled position 34. The ferrule receiving aperture 56 of the guide tip 54 is aligned with a movement path 36 of the ferrule engaging end 26 of the needle 24 when the guide tip 54 is in the enabled position 34. The ferrule receiving aperture 56 of the guide tip 54 is not aligned with the movement path 36 of the ferrule engaging end 26 of the needle 24 when the guide tip 54 is in the retracted position 32. In this embodiment, the ferrule receiving aperture 56 is not aligned parallel with the movement path 36 of the ferrule engaging end 26 of the needle 24 when the guide tip 54 is in the retracted position 32. The guide tip 54 is moveably coupled to the shaft 22 for selectable movement between the retracted position 32 and the enabled position 34. In the embodiment of FIG. 1C, such movement includes a rotational or pivoting action to align the ferrule receiving aperture 56 of the guide tip 54 with the needle movement path 36.

The ferrule engaging end 26 of the needle 24 and the ferrule receiving aperture 56 may be configured by those skilled in the art to cooperate with a suture having a ferrule attached to one end as described previously. As with the previous embodiment, the device 52 of FIG. 1C has a smaller insertion profile 58 when the guide tip 54 is in the retracted position 32, than the insertion profile 60 corresponding to when the guide tip 54 is in the enabled position 34. As with previous embodiments, since the insertion profile 58 is smaller in the retracted position 32 than the insertion profile 60 in the engaged position, the device 52 can be used with a smaller minimally invasive entry point than would be required for a non-retractable device.

Figure 2A:
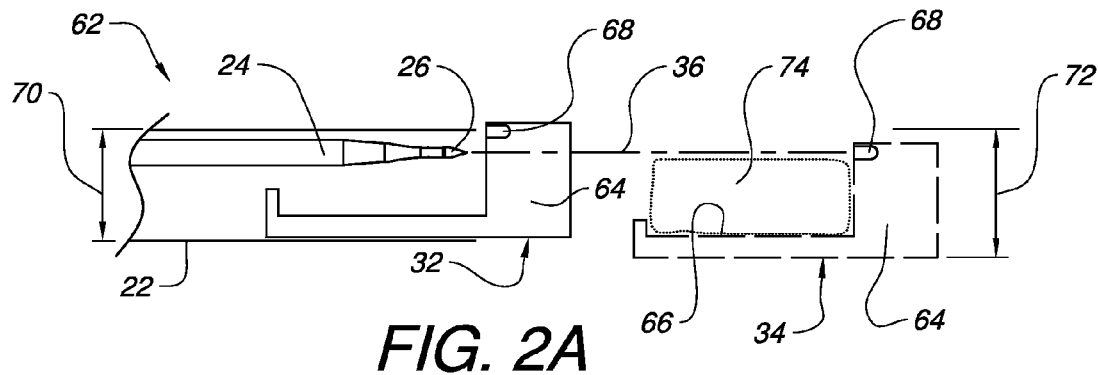
FIGS. 2A-2B schematically illustrate examples of a minimally invasive surgical suturing device having embodiments of a guide tip with a tissue engaging surface.

FIG. 2A schematically illustrates another example of a minimally invasive surgical suturing device 62, in this instance, having an embodiment of a guide tip 64 with a tissue engaging surface 66. The suturing device 62 has a shaft 22. The suturing device 62 also has a needle 24 which is slideably coupled to the shaft 22 and has a ferrule engaging end 26. The needle 24 is preferably slideable in directions substantially parallel to the shaft 22. As with previous embodiments, the guide tip 64 has a ferrule receiving aperture 68. The guide tip 64 is moveably coupled to the shaft 22 for selectable movement between a retracted position 32 and an enabled position 34. The ferrule receiving aperture 68 of the guide tip 64 is aligned with a movement path 36 of the ferrule engaging end 26 of the needle 24 when the guide tip 64 is in the enabled position 34.

The ferrule engaging end 26 of the needle 24 and the ferrule receiving aperture 68 may be configured by those skilled in the art to cooperate with a suture having a ferrule attached to one end as described previously. As with the previous embodiment, the device 62 of FIG. 2A has a smaller insertion profile 70 when the guide tip 64 is in the retracted position 32, than the insertion profile 72 corresponding to when the guide tip 64 is in the enabled position 34.

The tissue engaging surface 66 defines a tissue bite area 74 in conjunction with the travel path 36 of the needle. In this embodiment, the tissue bite area 74 is larger in the enabled position 34 than when the guide tip 64 is in the retracted position 32 because the tissue engaging surface 66 is moved away from the travel path 36 of the ferrule engaging end 26 of the needle 24. The larger tissue bite area 74 in the enabled position 34 has the advantage of facilitating better placement of suture stitches when working with tissue in a body cavity while still being able to retract to a smaller insertion profile for entry and exit of the guide tip end of the device 62 to and from the body cavity.

Figure 2B:
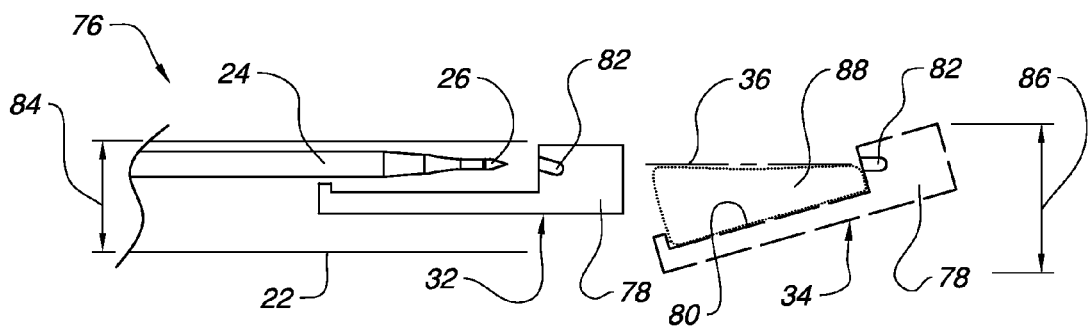

Similarly, FIG. 2B schematically illustrates another example of a minimally invasive surgical suturing device 76, in this instance, having an embodiment of a guide tip 78 with a tissue engaging surface 80. The suturing device 76 has a shaft 22. The suturing device 76 also has a needle 24 which is slideably coupled to the shaft 22 and has a ferrule engaging end 26. The needle 24 is preferably slideable in directions substantially parallel to the shaft 22. As with previous embodiments, the guide tip 78 has a ferrule receiving aperture 82. The guide tip 78 is moveably coupled to the shaft 22 for selectable movement between a retracted position 32 and an enabled position 34. The ferrule receiving aperture 82 of the guide tip 78 is aligned with a movement path 36 of the ferrule engaging end 26 of the needle 24 when the guide tip 78 is in the enabled position 34. In this embodiment, the ferrule receiving aperture 82 is not aligned parallel with the movement path 36 of the ferrule engaging end 26 of the needle 24 when the guide tip 78 is in the retracted position 32. As mentioned, the guide tip 78 is moveably coupled to the shaft 22 for selectable movement between the retracted position 32 and the enabled position 34. In the embodiment of FIG. 2B, such movement includes a rotational or pivoting action to align the ferrule receiving aperture 82 of the guide tip 78 with the needle movement path 36.

The ferrule engaging end 26 of the needle 24 and the ferrule receiving aperture 82 may be configured by those skilled in the art to cooperate with a suture having a ferrule attached to one end as described previously. The suturing device 76 of FIG. 2B has a smaller insertion profile 84 when the guide tip 78 is in the retracted position 32, than the insertion profile 86 corresponding to when the guide tip 78 is in the enabled position 34.

Similar to the previous embodiment, the tissue engaging surface 80 defines a tissue bite area 88 in conjunction with the travel path 36 of the needle. In this embodiment, the tissue bite area 88 is larger in the enabled position 34 than when the guide tip 78 is in the retracted position 32 because the tissue engaging surface 80 is moved and/or pivoted away from the travel path 36 of the ferrule engaging end 26 of the needle 24. The larger tissue bite area 88 in the enabled position 34 has the advantage of facilitating better placement of suture stitches when working with tissue in a body cavity while still being able to retract to a smaller insertion profile for entry and exit of the guide tip end of the device 76 to and from the body cavity.

Figure 3:
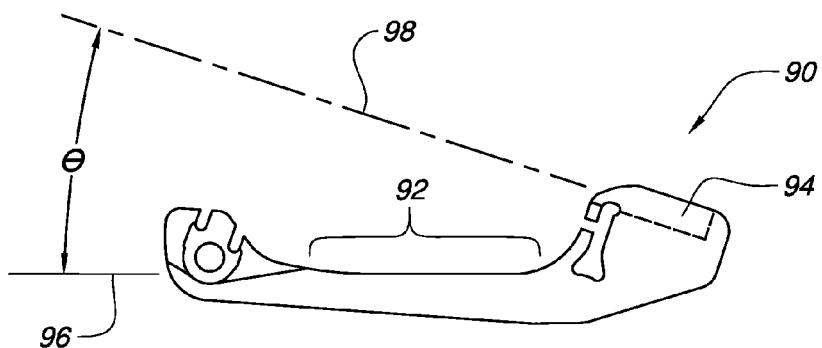
FIG. 3 illustrates one example of a guide tip having one embodiment of an orientation between a tissue engaging surface and a ferrule receiving aperture.

FIG. 3 illustrates one example of a guide tip 90 having one embodiment of an orientation between a tissue engaging surface 92 and a ferrule receiving aperture 94. In this embodiment, the tissue engaging surface substantially lies in a plane 96 (illustrated as line 96 in this two-dimensional view) that forms an acute angle θ with a center line 98 of the ferrule receiving aperture 94 on the tissue engaging surface 92 side of the guide tip 90. Although many angles are possible between the center line 98 and the plane 96, the angle θ is intended to be the minimum angle that can be formed between the center line 98 and the plane 96 as illustrated in the side view of FIG. 3.

Figure 4A:
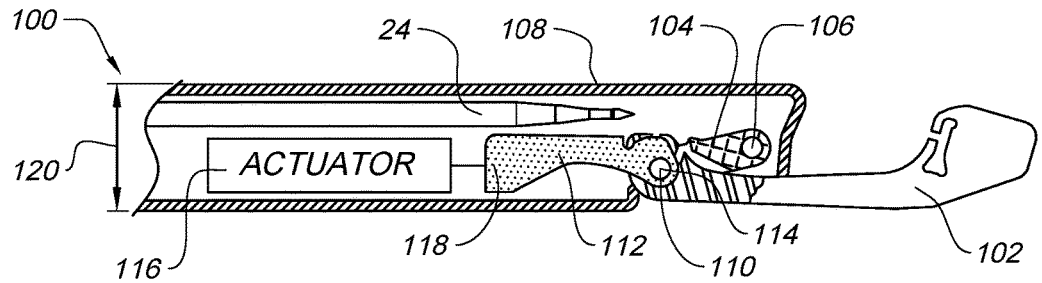
FIGS. 4A-4C are partial cross-sectional and schematic views of one embodiment of a minimally invasive surgical suturing device having a guide tip that is actuated to move from a retracted position to an enabled position.
Figure 4B:
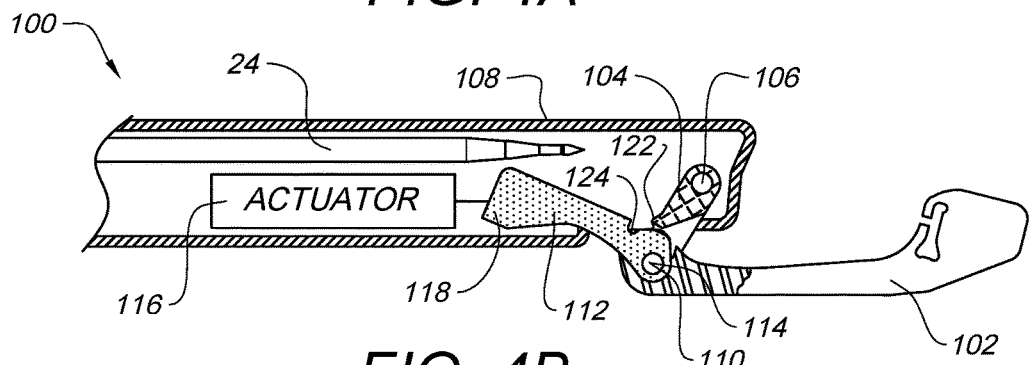
Figure 4C:
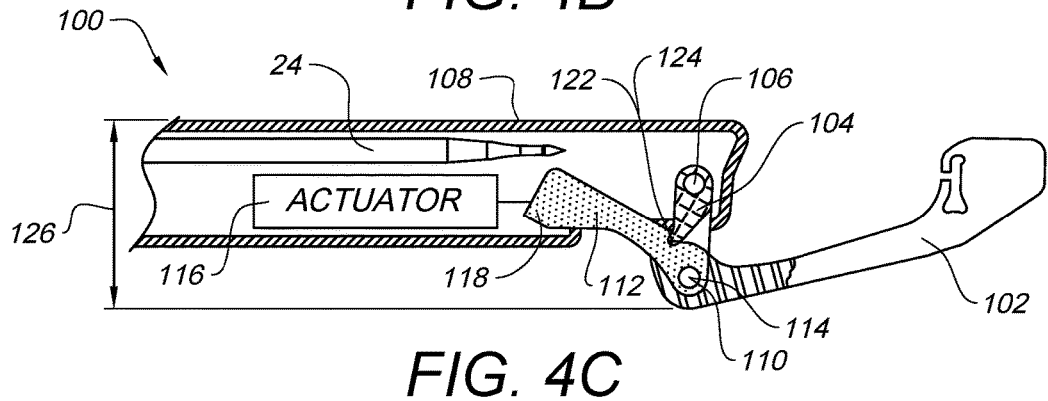

FIGS. 4A-4C are partial cross-sectional and schematic views of one embodiment of a minimally invasive surgical suturing device 100 having a guide tip 102 that is schematically actuated to move from the retracted position illustrated in FIG. 4A to the enabled position illustrated in FIG. 4C. The guide tip 102 has an embodiment of a linkage that includes a drive yoke 104 pivotally coupled at a first end 106 of the drive yoke 104 to the shaft 108 and pivotally coupled at a second end 110 of the drive yoke 104 to the guide tip 102. The illustrated embodiment of a linkage also includes a drive link 112 which is pivotally coupled at a first end 114 of the drive link 112 to the point 110 where the drive yoke 104 and the guide tip 102 are pivotally coupled. The linkage may also include or be coupled to an actuator 116 coupled to a second end 118 of the drive link 112. The actuator 116 is illustrated schematically because it is well within the abilities of those skilled in the art to implement a variety of actuators 116, coupled to the second end 118 of drive link 112, and configured to move the drive link 112 as described below. The actuator 116 may include one or more of the following non-limiting elements: a cable, a rod, a lever, a knob, a dial, a motor, and a solenoid.

In FIG. 4A, the guide tip 102 is in a retracted position having a first insertion profile 120. In this embodiment, movement of the actuator 116 that pushes the second end 118 of the drive link 112 toward the guide tip 102 will cause the point 110, 114 where the guide tip 102 is coupled to the first end 114 of the drive link 112 and the second end 110 of the drive yoke 104, to swing out of an opening in the shaft 108 as illustrated in FIG. 4B.

The drive yoke 104 may have a cam protrusion 122 oriented to engage a follower notch 124 as the actuator 116 continues to push the second end 118 of the drive link 112 toward the guide tip 102. The cam 122 of the drive yoke 104 and the follower 124 of the drive link 112 will contact each other to help stabilize the guide tip 102 as it reaches the enabled position illustrated in FIG. 4C. As also shown in FIG. 4C, the engaged position insertion profile 126 is larger than the retracted position insertion profile 120 of FIG. 4A. By reversing the sequence of FIGS. 4A-4C, it can also be seen that a movement of the actuator 116 that pulls the second end 118 of the drive link 112 away from the guide tip 102 will cause the guide tip 102 to move toward the retracted position of FIG. 4A when starting in the enabled position of FIG. 4C.

Figure 4D:
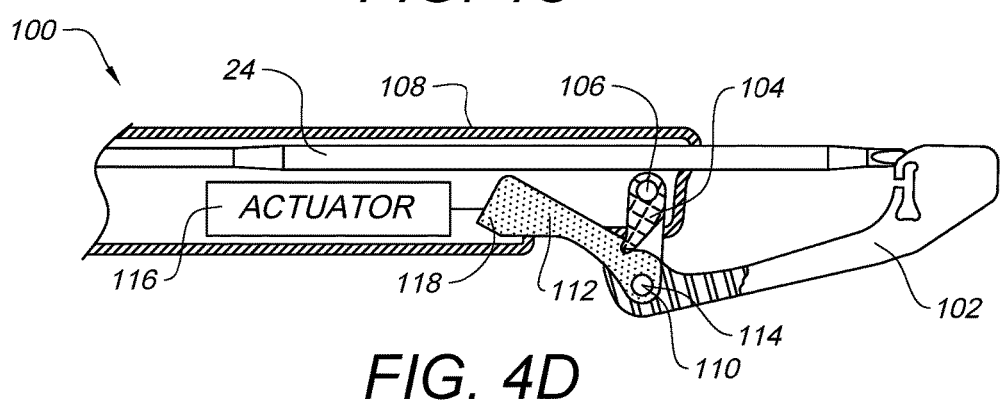
FIG. 4D illustrates advancement of a needle in alignment with a ferrule receiving aperture when the device of FIGS. 4A-4C is in the enabled position.

Once the device 100 is in the enabled position of FIG. 4C, the needle 24 can be advanced in alignment with a ferrule receiving aperture (not visible in this view, but discussed in previous embodiments) as illustrated in FIG. 4D. Methods of advancement and retraction of the needle 24 for suturing with a suture thread having a ferrule are known to those skilled in the art, and have been discussed previously, for example with regard to U.S. Pat. No. 7,211,093 which is incorporated herein by reference in its entirety.

Figure 5:
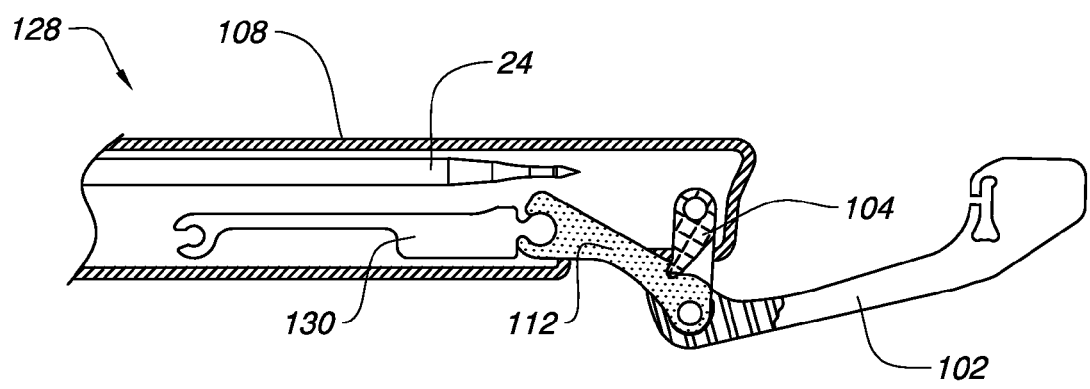
FIG. 5 is a partial cross-sectional view of one example of a minimally invasive surgical suturing device illustrating one embodiment of an actuator coupled to a linkage that moves a guide tip from a retracted position to an enabled position.

FIG. 5 is a partial cross-sectional view of another example of a minimally invasive surgical suturing device 128. The embodiment of FIG. 5 is similar to the embodiment of FIGS. 4A-4D, discussed above, except that the actuator comprises a flex link 130 which may be utilized by those skilled in the art to couple a cable or other flexible actuator to the linkage. Other embodiments may use other types of connectors to couple the actuation mechanisms to the linkage. Such embodiments and their equivalents will be apparent to those skilled in the art and are intended to be covered in the scope of the appended claims.

FIG. 6 illustrates another embodiment of a minimally invasive surgical suturing device 132 having another embodiment of an actuator 134 for moving a guide tip 102 between retracted (as illustrated) and engaged positions. In this embodiment, the shaft 108 (shown in broken form for clarity of the entire device) is coupled at a proximal end to a handle 136. The handle 136 has a grip 137. The actuator 134 in this embodiment includes a knob 134 which those skilled in the art will readily see may be rotatably coupled to the linkage (not shown, but discussed previously) that moves the guide tip 102 between a retracted position and an engaged position. For example, rotation of the actuator 134 in a first direction may cause the guide tip 102 to move toward the enabled position when starting in the retracted position. Similarly, rotation of the actuator 134 in a second direction, opposite the first direction, may cause the guide tip 102 to move toward the retracted position when starting in the enabled position. The suturing device 132 may also have a lever 138 configured to advance the needle on a path substantially parallel to the shaft, toward and in alignment with the ferrule receiving aperture as discussed for the embodiments above.

Figure 7B:
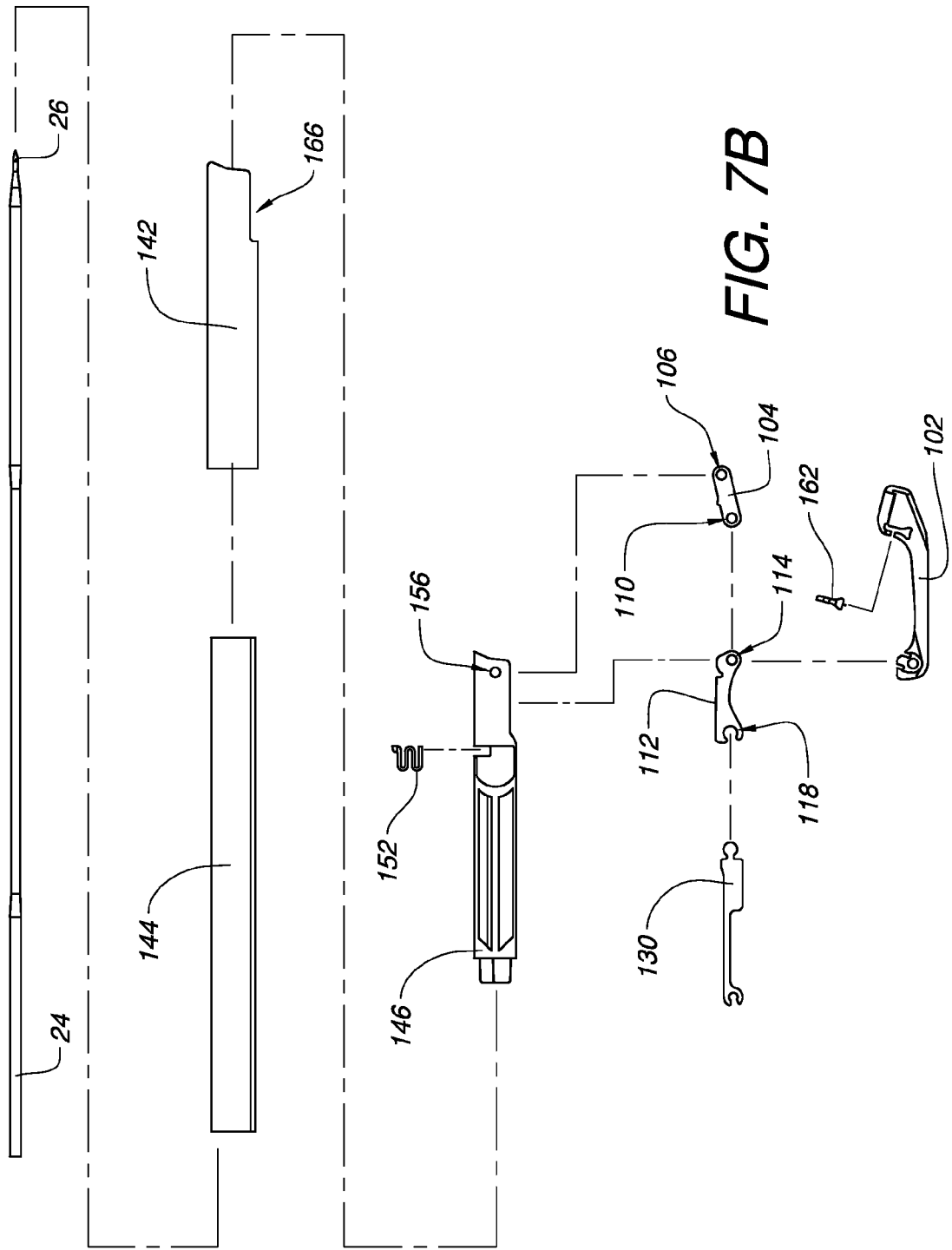
FIG. 7B is an exploded side view of the minimally invasive surgical suturing device from FIG. 7A.

FIGS. 7A and 7B are exploded perspective and side views, respectively, of another embodiment of a minimally invasive surgical suturing device 140. The functionality and interaction of the guide tip 102, the drive yoke 104, and the drive link 112, have been discussed previously with regard to FIGS. 4A-4D. Similarly, the functionality of the needle 24 has been discussed above. The embodiment of FIGS. 7A and 7B offer additional details for how the drive yoke 104 may be moveably coupled to the shaft. In this embodiment, the shaft includes, but is not limited to an outer tube 142, a guide 144, and an inner body 146. The guide 144 has a needle groove 148 sized to slideably receive the needle 24 and guide its movement in a direction substantially parallel to the shaft. The guide 144 couples against the inner body 146 which has a corresponding needle groove 150 for continued guidance of the needle 24. In some embodiments, the guide 144 and the inner body 146 could be a single piece.

In this embodiment, the inner body 146 is configured to hold a ferrule release spring 152. The ferrule release spring 152 has an upper blade 154 which rides below and is biased against the needle 24 while the needle 24 slides in the groove 150 of the inner body 146. When a surgeon has finished suturing with the suturing device 140, the suture will be trimmed, leaving a portion of excess suture and its ferrule still attached to the ferrule engaging end 26 of the needle 24. At this point, the needle 24 may be pulled back in the groove farther than its normal travel, causing the upper blade 154 of the ferrule release spring 152 to engage an edge of the ferrule, causing it to release from the needle 24.

The drive yoke 104 is pivotally coupled at a first end 106 of the drive yoke to the inner body 146 of the shaft at pivot point 156. The drive yoke 104 is also pivotally coupled at a second end 110 of the drive yoke to the guide tip 102. The drive link 112 is pivotally coupled at a first end 114 of the drive link 112 to the point 110 where the drive yoke 104 and the guide tip 102 are pivotally coupled. This embodiment also includes a flex link 130 coupled to a second end 118 of the drive link 112 as discussed previously. The inner body 146 has a linkage groove 158 to help guide and make room for movement of the linkage. Similarly, the guide 144 has a corresponding linkage groove 160 which can guide a cable, rod, or similar mechanism for actuation of the linkage.

As shown in FIGS. 7A and 7B, the embodied suturing device 140 also includes a tip latch spring 162 that is inserted into the guide tip 102 adjacent to the ferrule receiving aperture 94. The tip latch spring 162 has a tip latch blade 164 which is biased against the ferrule engaging end 26 of the needle 24 when the needle 24 is alternately advanced and pulled back to pick up and drop off the suture ferrule during operation. The suture ferrule, having a larger diameter than the ferrule engaging end 26 of the needle 24 will just ride over the tip latch blade 164 when the ferrule is being returned to the guide tip. However, the ferrule engaging end 26 of the needle 24 is stepped on at least one side so that retraction of the needle 24 will cause a ferrule attached to the ferrule engaging end 26 of the needle 24 to catch on the tip latch blade 164 and release from the needle 24. On a return trip, the needle 24 may be rotated so that an unstepped side of the needle rides over the tip latch blade 164 to pick up the ferrule. This time, the ferrule engaging end 26 of the needle 24 is pressed into a holding contact with the ferrule, and as the needle 24 is withdrawn, the combined needle/ferrule ride smoothly over the tip latch blade 164 without releasing the ferrule. The cycle can be repeated as desired and the suturing device 140 can be used for suturing in this fashion.

The outer tube 142 of the shaft may be sized to cover one or more portions of the inner body 146 and the guide 144. Additional and/or longer tube pieces may be provided, depending on the embodiment. As can be seen in the side view of FIG. 7B, the outer tube 142 may include a notch or opening 166 to allow room for the linkage and guide tip 102 to swing out into the engaged position as described above.

FIGS. 8A-8C illustrate a time sequence highlighting one advantage of the disclosed embodiments for a minimally invasive surgical suturing device, namely the ability to utilize a guide tip and shaft having a larger insertion profile than an access dimension of a minimally invasive entry point. FIGS. 8A-8C schematically illustrate one or more tissue layers 168 into which a minimally invasive entry point 170, such as a cannula, has been installed. The minimally invasive entry point 170 has an inner dimension 172. The space above the illustrated tissue 168 is considered to be outside of a body and the space below the illustrated tissue 168 is considered to be inside a body cavity. In FIG. 8A, an embodiment of a minimally invasive surgical suturing device 174 is shown outside of the body in a retracted position. The insertion profile 176 of the guide tip and shaft in the retracted position is no larger than the entry point dimension 172. This allows the surgical suturing device 174 to be inserted into the minimally invasive entry point 170 as illustrated in FIG. 8B. Once the distal end of the shaft, having the guide tip in the retracted position, has passed through the minimally invasive entry point 170 and into the body cavity, the guide tip may be actuated into an enabled position as described above and as schematically illustrated in FIG. 8C.

Figure 9:
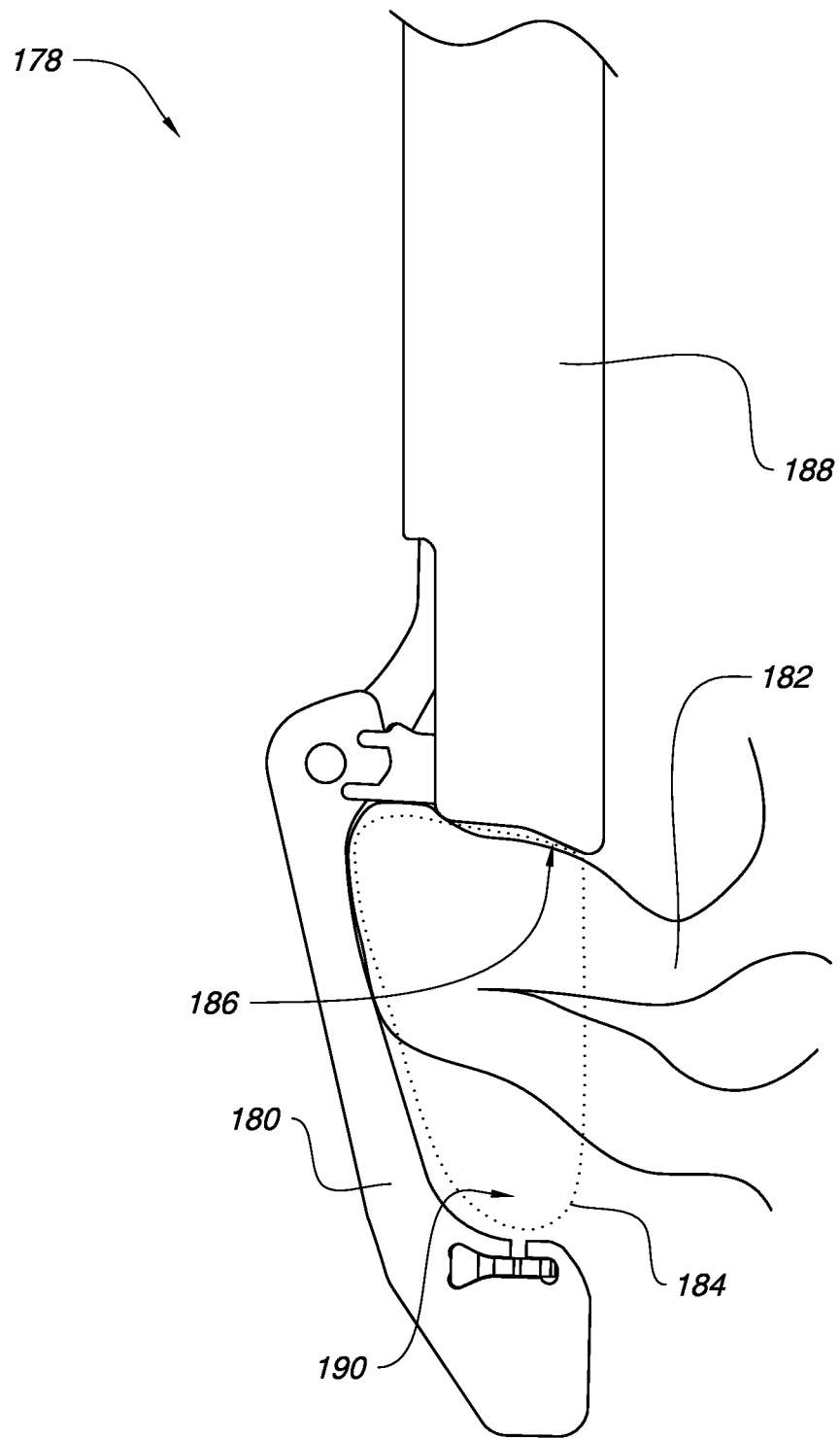
FIG. 9 illustrates an example of a minimally invasive surgical suturing device having an embodiment of a guide tip with an orientation configured to guide tissue in a bite area toward a portion of the bite area where a needle slides out of the shaft and toward a ferrule receiving aperture.

FIG. 9 illustrates an example of a minimally invasive surgical suturing device 178 having an embodiment of a guide tip 180 with an orientation configured to guide tissue 182 in a bite area 184 toward a portion 186 of the bite area 184 where a needle slides out of the shaft 188 and toward a ferrule receiving aperture (not visible in this view). This orientation is possible because the bite area 184 is wider near the portion 186 where the needle slides out of the shaft than near the end 190 of the guide tip 180. This enables more accurate control over suture placement.

Figure 10:
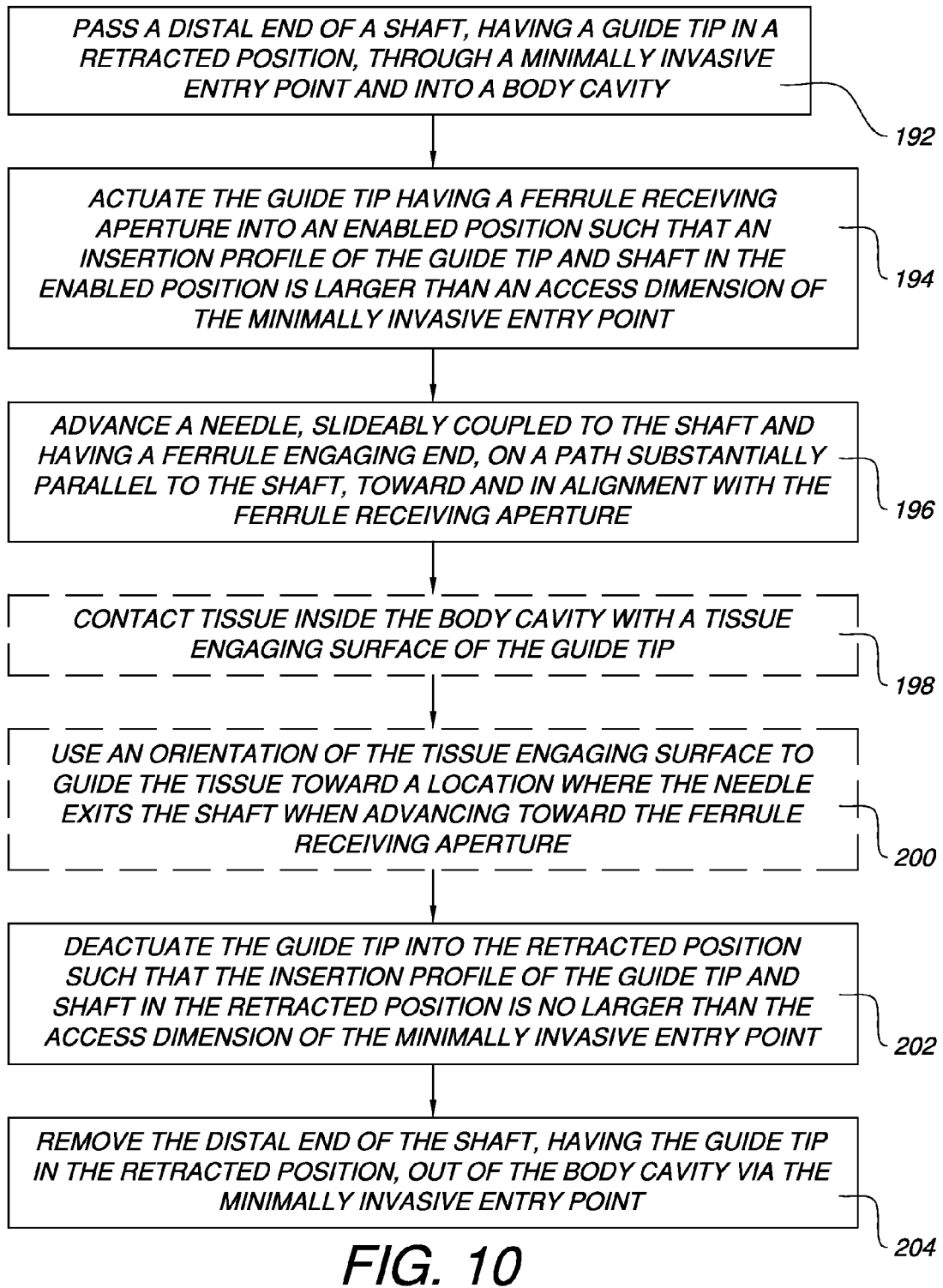
FIG. 10 illustrates one embodiment of a minimally invasive surgical suturing method.

FIG. 10 illustrates one embodiment of a minimally invasive surgical suturing method. In step 192, a distal end of a shaft, having a guide tip in a retracted position, is passed through a minimally invasive entry point and into a body cavity. In step 194, the guide tip having a ferrule receiving aperture is actuated into an enabled position such that an insertion profile of the guide tip and shaft in the enabled position is larger than an access dimension of the minimally invasive entry point. In step 196, a needle, slideably coupled to the shaft and having a ferrule engaging end, is advanced on a path substantially parallel to the shaft, toward and in alignment with the ferrule receiving aperture. As discussed with regard to the previous embodiments, the movement path of the needle does not necessarily need to be aligned with the ferrule receiving aperture when the guide tip is in the retracted position.

In optional steps 198 and 200, tissue inside the body cavity is contacted with a tissue engaging surface of the guide tip; and an orientation of the tissue engaging surface is used to guide the tissue toward a location where the needle exits the shaft when advancing toward the ferrule receiving aperture.

In step 202, the guide tip is deactuated into the retracted position such that the insertion profile of the guide tip and shaft in the retracted position is no larger than the access dimension of the minimally invasive entry point. In step 204, the distal end of the shaft, having the guide tip in the retracted position, is removed out of the body cavity via the minimally invasive entry point.

Various advantages of minimally invasive surgical suturing device and method have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. As just one example, other embodiments may include more than one needle and a corresponding number of ferrule receiving apertures. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:
1. A minimally invasive surgical suturing device, comprising:
   a shaft;
   a needle slideably coupled to the shaft and having a ferrule engaging end; and
   a guide tip having a ferrule receiving aperture and moveably coupled to the shaft for selectable movement between a retracted position and an enabled position; and a linkage moveably coupling the guide tip to the shaft, the linkage comprising:
a drive yoke pivotally coupled at a first end to the shaft and pivotally coupled at a second end to the guide tip;
a drive link pivotally coupled at a first end to the point where the drive yoke and the guide tip are pivotally coupled; and
an actuator coupled to a second end of the drive link.

2. The minimally invasive surgical suturing device of claim 1, wherein the actuator comprises a flex link.

3. The minimally invasive surgical suturing device of claim 1, wherein the actuator comprises at least one element selected from the group consisting of a cable, a rod, a lever, a knob, a dial, a motor, and a solenoid.

4. The minimally invasive surgical suturing device of claim 1, wherein:
a movement of the actuator that pushes the second end of the drive link toward the guide tip causes the guide tip to move toward the enabled position when starting in the retracted position; and
a movement of the actuator that pulls the second end of the drive link away from the guide tip causes the guide tip to move toward the retracted position when starting in the enabled position.

5. A minimally invasive surgical suturing device, comprising:
a) a shaft;
b) a needle slideably coupled to the shaft and having a ferrule engaging end;
c) a guide tip having a tissue engaging surface and a ferrule receiving aperture, the guide tip moveably coupled to the shaft for selectable movement between a retracted position and an enabled position;
d) a linkage moveably coupling the guide tip to the shaft, the linkage comprising:
1) a drive yoke pivotally coupled at a first end to the shaft and pivotally coupled at a second end to the guide tip;
2) a drive link pivotally coupled at a first end to the point where the drive yoke and the guide tip are pivotally coupled; and
3) an actuator coupled to a second end of the drive link; and
e) wherein:
1) the ferrule receiving aperture of the guide tip is not aligned with a movement path of the ferrule engaging end of the needle when the guide tip is in the retracted position;
2) the ferrule receiving aperture of the guide tip is aligned with the movement path of the ferrule engaging end of the needle when the guide tip is in the enabled position;
3) the tissue engaging surface of the guide tip defines a tissue bite area in conjunction with the movement path of the ferrule engaging end of the needle;
4) the tissue bite area is larger when the guide tip is in the enabled position than when the guide tip is in the retracted position;
5) a movement of the actuator that pushes the second end of the drive link toward the guide tip causes the guide tip to move toward the enabled position when starting in the retracted position; and
6) a movement of the actuator that pulls the second end of the drive link away from the guide tip causes the guide tip to move toward the retracted position when starting in the enabled position.

* * * * *